(12) United States Patent
Smith et al.

(10) Patent No.: US 6,544,942 B1
(45) Date of Patent: Apr. 8, 2003

(54) PHASE-SEPARATING SOLVENT COMPOSITION

(75) Inventors: Kim R. Smith, Woodbury, MN (US); Mark D. Levitt, Saint Paul, MN (US); Robert D. P. Hei, Baldwin, WI (US)

(73) Assignee: Ecolab Inc., Saint Paul, MN (US)

( * ) Notice: Subject to any disclaimer, the term of this patent is extended or adjusted under 35 U.S.C. 154(b) by 112 days.

(21) Appl. No.: 09/641,775

(22) Filed: Aug. 18, 2000

Related U.S. Application Data

(63) Continuation-in-part of application No. 09/560,170, filed on Apr. 28, 2000.

(51) Int. Cl.$^7$ ................................................. C11D 3/44
(52) U.S. Cl. ...................... 510/417; 510/365; 510/506
(58) Field of Search ................... 510/365, 417, 510/206, 284, 506; 134/10

(56) References Cited

U.S. PATENT DOCUMENTS

| | | | |
|---|---|---|---|
| 4,130,435 A | * 12/1978 | Hall | |
| 4,414,128 A | 11/1983 | Goffinet | ...................... 252/111 |
| 4,592,787 A | 6/1986 | Johnson | |
| 4,689,168 A | * 8/1987 | Requejo | |
| 4,891,073 A | 1/1990 | Shortt et al. | ................... 134/20 |
| 4,992,108 A | 2/1991 | Ward et al. | |
| 5,007,969 A | 4/1991 | Doscher | |
| 5,080,822 A | 1/1992 | VanEenam | |
| 5,080,831 A | 1/1992 | VanEenam | |
| 5,096,501 A | * 3/1992 | Dishart et al. | |
| 5,158,710 A | 10/1992 | VanEenam | |
| 5,342,551 A | 8/1994 | Ruckle | |
| 5,419,848 A | 5/1995 | VanEenam | |
| 5,529,887 A | 6/1996 | Horn et al. | |
| 5,585,341 A | 12/1996 | VanEenam | |
| 5,637,559 A | 6/1997 | Koreltz et al. | |
| 5,744,440 A | 4/1998 | Liu | |
| 5,786,319 A | 7/1998 | Pedersen et al. | |
| 5,811,383 A | 9/1998 | Klier et al. | |
| 5,849,682 A | 12/1998 | VanEenam | |
| 5,854,187 A | 12/1998 | Blum et al. | |
| 5,922,665 A | 7/1999 | Liu | |
| 5,972,874 A | 10/1999 | Libutti et al. | |
| 5,997,042 A | 12/1999 | Hernandez et al. | |
| 6,010,995 A | 1/2000 | VanEenam | |

FOREIGN PATENT DOCUMENTS

| | | |
|---|---|---|
| DE | 198 11 386 A1 | 9/1999 |
| GB | 2 173 508 A | 10/1986 |
| WO | WO 94/22965 | 10/1994 |
| WO | WO 97/18285 | 5/1997 |
| WO | WO 98/11168 | 3/1998 |

OTHER PUBLICATIONS

Industrial Solvents Handbook, $2^{nd}$ edition, Noyes Data Corporation, 1977, NJ, USA, p. 352.*

Product Information Sheet, "*Solder Seal® Gunk® Hydroseal II Heavy Duty Cold Parts Cleaner,*" Radiator Specialty Company, Charlotte, NC (Mar. 1997).

Material Safety Data Sheet for 'Upper Limits,' Spartan Chemical Company, Inc., Jan. 12, 1990.

Material Safety Data Sheet for 'Hydro Seal II Heavy Duty Cold Parts Cleaner,' Radiator Specialty Company, Aug. 1998.

* cited by examiner

*Primary Examiner*—Gregory E. Webb
(74) *Attorney, Agent, or Firm*—IPLM Group, P. A.

(57) ABSTRACT

A pseudo-stable phase-splitting solvent composition that forms a single liquid phase when subjected to mild agitation and retains that single phase while the composition is applied to a surface, but which forms two or more laminar liquid phases promptly after being applied. A concentrated solvent film forms on the surface, under a film containing the other phase. The solvent preferably is denser than water, and the composition preferably is diluted with water. This enables the solvent to attack the surface at near full strength, and provides a water seal over the solvent film.

The solvent composition can be used full strength or in diluted form for cleaning, reducing the microbial population of, or degreasing a variety of surfaces, and for stripping a variety of difficult-to-remove coatings from surfaces.

25 Claims, No Drawings

PHASE-SEPARATING SOLVENT COMPOSITION

CROSS-REFERENCE TO RELATED APPLICATION

This application is a continuation-in-part of application Ser. No. 09/560,170, filed Apr. 28, 2000 pending.

TECHNICAL FIELD

This invention relates to solvent compositions that can be used, for example, to clean, reduce the microbial population of, or degrease soiled surfaces, or to strip floor finishes or other coatings from coated surfaces.

BACKGROUND

Many concentrates and ready-to-use compositions have been proposed for cleaning, degreasing and stripping purposes. For example, U.S. Pat. No. 5,080,822 (VanEenam '822); U.S. Pat. No. 5,080,831 (VanEenam '831); U.S. Pat. No. 5,158,710 (VanEenam '710); U.S. Pat. No. 5,419,848 (VanEenam '848); U.S. Pat. No. 5,585,341 (VanEenam '341); U.S. Pat. No. 5,849,682 (VanEenam '682); and U.S. Pat. No. 6,010,995 (VanEenam '995) describe various compositions for cleaning, degreasing or stripping. These compositions are said to be stable clear solutions, stable emulsions or stable microemulsions.

U.S. Pat. No. 4,592,787 (Johnson) describes an aqueous photoresist stripping composition containing a lower alkyl mono ether of a propylene glycol, a $C_{2-6}$ alkanol, and alkanol amine, and a base. Stripping is carried out at a temperature at which the stripper composition is a single phase, and below a temperature at which the composition would undergo phase separation.

U.S. Pat. No. 5,529,887 (Horn et al.) describes an aqueous photoresist developer solution containing a diglycol monoalkyl ether, a glycol monoalkyl ether, an alkali hydroxide, and alkaline fluoride, and water.

U.S. Pat. No. 5,637,559 (Koreltz et al.) describes compositions for removing urethane/acrylic floor finishes. In diluted form, the compositions contain a phenyl-substituted alcohol, coupler and water, wherein the amount of the coupler is at least threefold the amount necessary to completely solubilize the phenyl-substituted alcohol in the water.

U.S. Pat. No. 5,744,440 (Liu '440) describes a mixture of a very slightly water-soluble organic solvent and an excess of an amine oxide coupler to fully solubilize the solvent, for hydrophobic soil and soap scum removal.

U.S. Pat. No. 5,786,319 (Pedersen et al.) describes a detergent formulation made from a glycol ether mixed with a high concentration of a surfactant, stably dispersed in water.

U.S. Pat. No. 5,811,383 (Klier et al.) describes oil continuous microemulsions containing water, one or more organic solvents and an anionic surfactant.

U.S. Pat. No. 5,854,187 (Blum et al.) describes microemulsion concentrates containing a nonionic surfactant oil phase, a continuous aqueous phase, a polar organic solvent coupling agent and a combination of surfactants. The microemulsions are said to be thermodynamically and temperature stable liquid systems which, when mixed with water to an appropriate solution, will invert and form stable macroemulsions, producing a bloom or milky color in the dilution medium.

U.S. Pat. No. 5,922,665 (Liu '665) describes a composition said to be capable of removing hydrophobic soils, and containing nonionic surfactant, a very slightly water-soluble organic solvent and water. The composition is said to be translucent or hazy.

U.S. Pat. No. 5,972,874 (Libutti et al.) describes microemulsion cleaners that are said to be stable and to have a clear to slightly hazy appearance.

U.S. Pat. No. 5,997,042 (Hernandez et al.) describes a floor stripper concentrate containing a mixture of two types of solvents and an excess of a solubilizing coupler. The coupler is said to be capable of increasing the phase-stability of the stripper and the stripper is said to be stable both as a concentrate and when diluted.

UV light curable coating compositions typically provide a desirable combination of properties including rapid cure, high gloss and good durability. Due to these properties and their generally good scratch and detergent resistance, UV light curable coating compositions have been used as floor finishes. Eventually even a UV light cured floor finish will show the effects of wear, and will require removal and renewal. UV cured floor finishes generally are not regarded as being removable using conventional chemical floor stripping agents. Instead, more aggressive removal techniques such as floor sanding typically must be employed. This can cause potential dust problems in the workplace and can remove a portion of the underlying floor surface. This has discouraged the use of UV cured floor finishes, particularly on vinyl tile, vinyl sheeting and other resilient flooring materials.

SUMMARY OF THE INVENTION

The present invention provides, in one aspect, a pseudo-stable phase-splitting cleaning, antimicrobial, degreasing or stripping solvent composition. The term, "phase" refers to a homogeneous liquid portion that is present or that can form in a liquid system. The term "phases" refers to the presence of more than one phase in a heterogeneous liquid system. The term "pseudo-stable" refers to a composition that forms a single phase when subjected to mild mixing or other agitation and retains that single phase for a sufficient period of time so that the composition can be applied to a surface, but which will promptly form two or more phases when left undisturbed. The term "phase-splitting" is meant to describe a single phase solvent composition that forms at least two laminar phases promptly after being applied atop a generally horizontal surface or on a generally vertical surface, whereby a film containing a concentrated amount of the solvent lies between the surface and a film containing a much lower amount of the solvent. The term "solvent" refers to an organic material or mixture of such materials suitable for cleaning, degreasing or stripping the desired surface. In a composition that has undergone phase splitting, the phase containing a concentrated amount of the solvent will be referred to as the solvent phase, and the phase containing a much lower amount of the solvent will be referred to as the dilute phase or diluting phase.

When used atop floors or other generally horizontal surfaces, the solvent phase should be more dense than the dilute phase. When used on walls or other generally vertical surfaces, the solvent phase should have a greater tendency to cling to the surface than does the dilute phase, so that the dilute phase will be displaced from the surface by the solvent phase.

In another aspect, the invention provides a cleaning, degreasing or stripping solvent concentrate and instructions for mixing the concentrate with water, wherein the concentrate contains a sufficient amount of cosolvent or surfactant so that a pseudo-stable phase-splitting composition will form when the concentrate is mixed with water according to the instructions.

In a further aspect, the invention provides an antimicrobial solvent concentrate and instructions for mixing the concentrate with water, wherein the concentrate contains an antimicrobial or biocidal agent dissolved or dispersed in the solvent and a sufficient amount of cosolvent or surfactant so that a pseudo-stable phase-splitting composition will form when the concentrate is mixed with water according to the instructions.

In a further aspect, the invention provides a split-phase cleaning, antimicrobial, degreasing or stripping agent atop a surface, wherein a non-aqueous film phase comprising a solvent that is denser than water lies adjacent the surface and under an aqueous film phase. This enables the solvent film to attack the surface at near full strength, and provides a water seal over the solvent film.

In another aspect, the invention provides a method of removing a coating or a soil from a surface, comprising applying to the surface a pseudo-stable mixture containing water, polar solvent that is denser than water, and a sufficient amount of cosolvent or surfactant so that the mixture phase-separates following application of the mixture to the surface, allowing the mixture to phase-separate, allowing the polar solvent to soften or dissolve the coating or soil, and removing the softened coating or soil.

In yet another aspect, the invention provides a method of removing soil from or reducing the antimicrobial population of a surface by contacting the surface with an aqueous dispersion of a solvent which forms split phases following contact with the surface, wherein a film phase containing primarily solvent lies adjacent the surface and under a film phase containing primarily water.

DETAILED DESCRIPTION

The solvent compositions of the invention can be applied to a variety of materials on a variety of surfaces. For example, the solvent compositions can be used to remove paints, finishes, photoresists, inks, oils, food soils and other coatings from a variety of surfaces, including hard surfaces and soft surfaces having smooth or porous topography. Suitable hard surfaces include, for example, architectural surfaces (e.g., floors, walls, windows, sinks, tables, counters and signs); eating utensils; hard-surface medical or surgical instruments and devices; hard-surface packaging; and transportation vehicles and vehicle components (e.g., automobiles, motorcycles, bicycles, and aircraft; and wheels, gears, engines and other parts therefor). Such hard surfaces can be made from a variety of materials comprising, for example, ceramics, metals, woods or hard plastics. Suitable soft surfaces include, for example, wallpaper; carpet; soft-surface medical or surgical instruments and devices; and soft-surface packaging. Such soft surfaces can be made from a variety of materials comprising, for example, paper, fiber, woven or nonwoven fabric or soft plastics. The compositions of the invention can also be applied to soft surfaces such as food substances and skin. In addition, the compositions of the invention can be used to reduce the microbial population of surfaces in areas such as kitchens, bathrooms, factories, hospitals, dental offices, food plants, etc.

When left undisturbed on a surface, the solvent compositions of the invention form two or more liquid film phases, with the solvent phase lying between the surface and the dilute phase. For example, on floors or other generally horizontal surfaces, the solvent phase will lie atop the floor (or atop a coating on the floor) and under the dilute phase or phases. On walls or other generally vertical surfaces, the solvent phase will lie adjacent the surface and under the dilute phase or phases.

For simplicity, the remainder of this specification will discuss compositions that form two-phase systems, it being understood that compositions forming three or more phases could be employed if desired.

Although a variety of materials could be used for the dilute phase or phases, preferably the dilute phase contains mainly water. The remainder of this specification will primarily discuss the use of water to form the dilute phase, it being understood that other suitable liquids could be substituted for water if desired.

The compositions of the invention preferably are formulated and sold as solvent concentrates. If desired, the concentrates can be used full-strength as a cleaner, antimicrobial agent, degreaser or stripper. However, the concentrates typically will be diluted with a liquid (e.g., water) that subsequently forms the dilute phase. Preferably the concentrate forms a single phase before such dilution and remains so while stored in the container in which it will be sold. When combined with water or other desired diluting liquid at an appropriate dilution level and subjected to mild agitation (e.g., by stirring the composition in a bucket, pumping, spraying or using a mop, cloth or other suitable implement), the compositions of the invention form a pseudo-stable solution or dispersion. The composition should remain in the pseudo-stable state for a sufficiently long period so that the composition can be applied to a surface before the onset of phase separation. The pseudo-stable state need only last for a few seconds when suitably rapid application techniques such as spraying are employed, or when agitation during application is employed. The pseudo-stable state desirably lasts for at least one minute or more after mixing and while the composition is stored in a bucket or other suitable vessel, and preferably lasts for five minutes or more after mixing. If a mop or other absorbent applicator, sprayer or pump is used to apply the compositions of the invention, then normal refilling or replenishment of the applicator (e.g., by dipping the mop in a mop bucket) will provide sufficient agitation of the composition to preserve its pseudo-stable state during application.

Following application to a surface, the composition undergoes phase-splitting. Preferably this will occur relatively soon after application, e.g., in less than 10 minutes, more preferably in less than 5 minutes and most preferably in less than 2 minutes.

The compositions of the invention are particularly preferred for use in stripping floor finishes. When so used, the compositions of the invention could be referred to as "strip agents". The strip agents of the invention are especially preferred for removing laminate floor finishes having a strippable intermediate coating on a substrate, and a strip agent-permeable coating or topcoat on the intermediate coating, wherein the topcoat is less strippable and more wear-resistant than the intermediate coating. In a preferred use for the strip agents of the invention, the substrate is a floor, the topcoat is a UV curable floor finish, the intermediate coating is an acrylic or urethane floor finish, and the strip agent contains benzyl alcohol.

The compositions of the invention can contain a variety of solvents. The solvent preferably is insoluble, or only sparingly soluble, in the diluting liquid. Thus for compositions intended to be diluted with water, the solvent preferably will have a water solubility less than about 5% by weight, more preferably less than about 3% by weight, and most preferably less than about 1% by weight (all parts and percentages in the remainder of this specification will be by weight unless otherwise indicated).

In general, the solvent is selected based upon the characteristics of the surface to which the solvent will be applied and upon the nature of the coating, soil or other material that will be contacted on and optionally removed from that surface. Polar solvents, or solvents capable of hydrogen bonding, typically will perform well on a variety of surfaces and materials and thus are preferred. For applications in which the solvent is intended to permeate through a durable overlayer or topcoat in order to attack and dissolve or soften an underlying layer, the solvent preferably has a high permeation rate through the overlayer. Compositions and methods employing such topcoats and underlying layers are described in the above-mentioned application Ser. No. 09/560,170, filed Apr. 28, 2000, and in application Ser. No. [Attorney Docket No. 103-1334.01], filed on even date herewith, both incorporated by reference herein. Preferably, the solvent also has a high flashpoint (e.g., greater than about 30° C., more preferably greater than about 50° C., and most preferably greater than about 100° C.), low odor and low toxicity.

Preferred solvents having a density greater than water (and thus especially useful in compositions that will be diluted with water and applied atop horizontal or generally horizontal surfaces) include acetamidophenol (specific gravity 1.027); acetanilide (specific gravity 1.219; water solubility <1%); acetophenone (specific gravity 1.0238; water solubility <1%); [2-acetyl-1-methylpyrrole (specific gravity 1.0413); benzyl acetate (specific gravity 1.0515; water solubility <1%); benzyl alcohol (specific gravity 1.0413; water solubility <1%); benzyl benzoate (specific gravity 1.118; water solubility <1%); benzyloxyethanol (specific gravity 1.07; water solubility <1%); ethers or hydroxyethers such as ethylene glycol phenyl ether (specific gravity 1.104; water solubility 2.3%; commercially available as "Dowanol EPh" from Dow Chemical Co.) and propylene glycol phenyl ether (specific gravity 1.063; water solubility 1.1%; commercially available as "Dowanol PPh" from Dow Chemical Co.); essential oils (e.g., benzaldehyde, pinenes (alphas, betas, etc.), terpineols, terpinenes, carvone, cinnamealdehyde, borneol and its esters, citrals, ionenes, jasmine oil, limonene, dipentene, linalool and its esters), dibasic esters such as dimethyl adipate, dimethyl succinate, dimethyl glutarate (often available in a mix with specific gravities greater than 1.00; including products available under the trade designations DBE, DBE-3, DBE-4, DBE-5, DBE-6, DBE-9, DBE-IB, and DBE-ME from DuPont Nylon), dimethyl malonate, diethyl adipate, diethyl succinate, diethyl glutarate, dibutyl succinate, and dibutyl glutarate; dialkyl carbonates such as dimethyl carbonate, diethyl carbonate, dipropyl carbonate, diisopropyl carbonate, and dibutyl carbonate; and phthalate esters such as dibutyl phthalate, diethylhexyl phthalate, and diethyl phthalate. Benzyl alcohol, essential oils, dibasic esters, dialkyl carbonates, ethylene glycol phenyl ether and propylene glycol phenyl ether are particularly preferred solvents. Mixtures of solvents can be used if desired.

The compositions of the invention should contain sufficient solvent to provide the desired rate and type of cleaning, microbial reduction, degreasing or stripping. Usually, solvent concentrates of the invention will contain at least about 5% solvent, preferably at least about 25% solvent, more preferably at least about 65% solvent, and most preferably about 75 to about 95% solvent.

The compositions of the invention can contain one or more cosolvents or surfactants to assist in providing the desired pseudo-stable and phase-splitting behavior. In general, cosolvents or surfactants that are relatively inefficient or ineffective (with respect to their ability to solubilize or disperse the solvent in the dilute phase) are preferred over cosolvents or surfactants that are more efficient or effective. This differs from the approach normally taken when formulating compositions containing cosolvents or surfactants. Normally, cosolvents and surfactants are selected for their ability to promote formation of stable solutions or dispersions.

A variety of cosolvents can be employed. In general, the cosolvent is selected based upon the characteristics of the chosen solvent and the solubility of the chosen solvent in the dilute phase. For compositions in which water serves as the dilute phase, the cosolvent generally will have higher water solubility than the water solubility of the chosen solvent. Preferably, the cosolvent has a high flashpoint (e.g., greater than about 30° C., more preferably greater than about 50° C., and most preferably greater than about 100° C.), low odor and low toxicity.

Preferred cosolvents include 2-(2-aminoethoxy)ethanol, monoethanolamine, diethanolamine, triethanolamine, amyl acetate, amyl alcohol, butanol, 3-butoxyethyl-2-propanol, butyl acetate, n-butyl propionate, cyclohexanone, diacetone alcohol, diethoxyethanol, diethylene glycol methyl ether, diethylene glycol n-butyl ether, diisobutyl carbinol, diisobutyl ketone, dimethyl heptanol, dipropylene glycol n-butyl ether, dipropylene glycol methyl ether, dipropylene glycol propyl ether, dipropylene glycol tert-butyl ether, ethanol, ethyl acetate, 2-ethylhexanol, ethyl propionate, ethylene glycol butyl ether, ethylene glycol methyl ether acetate, hexanol, isobutanol, isobutyl acetate, isobutyl heptyl ketone, isophorone, isopropanol, isopropyl acetate, methanol, methyl amyl alcohol, methyl n-amyl ketone, 2-methyl-1-butanol, methyl ethyl ketone, methyl isobutyl ketone, 1-pentanol, n-pentyl propionate, 1-propanol, n-propyl acetate, n-propyl propionate, propylene glycol n-butyl ether, propylene glycol ethyl ether, propylene glycol methyl ether, propylene glycol n-propyl ether, tripropylene glycol methyl ether and tripropylene glycol n-butyl ether. Ethylene glycol butyl ether and dipropylene glycol n-butyl ether are particularly preferred cosolvents. Mixtures of cosolvents can be used if desired.

Commercially available cosolvents (all of which are available from Union Carbide Corp.) include Butoxyethyl PROPASOL™, Butyl CARBITOL™ acetate, Butyl CARBITOL™, Butyl CELLOSOLVE™ acetate, Butyl CELLOSOLVE™, Butyl DIPROPASOL™, Butyl PROPASOL™, CARBITOL™ PM-600, CARBITOL™ Low Gravity, CELLOSOLVE™ acetate, CELLOSOLVE™, Ester EEP™, Filmer IBT™, Hexyl CARBITOL™, Hexyl CELLOSOLVE™, Methyl CARBITOL™, Methyl CELLOSOLVE™ acetate, Methyl CELLOSOLVE™, Methyl DIPROPASOL™, Methyl PROPASOL™ acetate, Methyl PROPASOL™, Propyl CARBITOL™, Propyl CELLOSOLVE™, Propyl DIPROPASOL™ and Propyl PROPASOL™.

The compositions of the invention preferably should not contain excessive amounts of cosolvent. Instead, the amount of cosolvent preferably is just sufficient to provide the desired pseudo-stable and phase-splitting behaviors. Larger amounts of cosolvent will tend to cause the composition to exhibit long term stability rather than pseudo-stability, and will delay (or prevent entirely) the attainment of split phases. Usually, the solvent concentrates of the invention will contain 0 to about 50% cosolvent, more preferably 0 to about 25% cosolvent, and most preferably 0 to about 20% cosolvent.

A variety of surfactants can be employed. In general, the surfactant's identity and use level is selected based upon the characteristics of the chosen solvent and the solubility of the chosen solvent in the dilute phase. For compositions in which water serves as the dilute phase, the surfactant preferably will have an HLB value greater than or equal to about 13, or less than or equal to about 6. This value reflects the above-noted preference for employing surfactants that are relatively inefficient or ineffective as emulsifiers. Preferably, the surfactant does not tend to cause formation of insoluble deposits, and has low odor and low toxicity. Mixtures of surfactants can be used if desired.

Preferred anionic surfactants include $C_6$–$C_{24}$ alkylbenzene sulfonates; $C_6$–$C_{24}$ olefin sulfonates; $C_6$–$C_{24}$ paraffin sulfonates; cumene sulfonate; xylene sulfonate; $C_6$–$C_{24}$ alcohol sulfates (preferably $C_6$–$C_{12}$ alcohol sulfates); and $C_6$–$C_{24}$ alcohol ether sulfates having 1 to about 20 ethylene oxide groups.

Preferred nonionic surfactants include $C_6$–$C_{24}$ alcohol ethoxylates (preferably $C_6$–$C_{14}$ alcohol ethoxylates) having 1 to about 20 ethylene oxide groups (preferably about 9 to about 20 ethylene oxide groups); $C_6$–$C_{24}$ alkylphenol ethoxylates (preferably $C_8$–$C_{10}$ alkylphenol ethoxylates) having 1 to about 100 ethylene oxide groups (preferably about 12 to about 20 ethylene oxide groups); and $C_6$–$C_{24}$ alkylpolyglycosides (preferably $C_6$–$C_{20}$ alkylpolyglycosides) having 1 to about 20 glycoside groups (preferably about 9 to about 20 glycoside groups).

Preferred cationic surfactants include quaternary amine compounds having the formula:

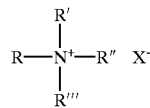

where R, R', R" and R'" are each an alkyl, aryl or aralkyl group that can optionally contain one or more P, O, S or N heteroatoms, and X is F, Cl, Br, I or an alkyl sulfate.

Preferred amphoteric surfactants include amine oxide compounds having the formula:

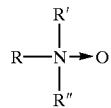

where R, R', R" and R'" are each a $C_6$–$C_{24}$ alkyl, aryl or aralkyl group that can optionally contain one or more P, O, S or N heteroatoms.

Another class of preferred amphoteric surfactants includes betaine compounds having the formula:

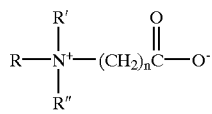

where R, R', R" and R'" are each a $C_6$–$C_{24}$ alkyl, aryl or aralkyl group that can optionally contain one or more P, O, S or N heteroatoms, and n is about 1 to about 10.

The compositions of the invention should not contain excessive amounts of surfactant. Instead, the amount of surfactant should be just sufficient to provide the desired pseudo-stable and phase-splitting behaviors. Larger amounts of surfactant will tend to cause the composition to exhibit permanent stability rather than pseudo-stability, will prolong (or prevent entirely) the attainment of split phases, and may cause the formation of undesirable deposits or other soils on the surface to which the compositions are applied. Usually, the solvent concentrates of the invention will contain no more than about 10% surfactant, more preferably 0 to about 3% surfactant and most preferably 0 to about 1% surfactant. Most preferably, the compositions of the invention are substantially surfactant-free.

The solvent compositions of the invention can optionally contain antimicrobial or biocidal agents that will dissolve or disperse in the solvent or dilute phase upon mixing. Desirably, the antimicrobial agent will preferentially dissolve or disperse in the solvent phase rather than in the dilute phase. Suitable antimicrobial agents include carboxylic acids (e.g., butyric acid, heptanoic acid, octanoic acid, nonanoic acid, and decanoic acid), sulfonic acids (e.g., dodecylbenzene sulfonic acid), active halogen compounds (e.g., sodium hypochlorite or sodium chlorite), active oxygen compounds (e.g., hydrogen peroxide, or equilibrium derived or isolated peracids such as peracetic acid, perheptanoic acid, peroctanoic acid, performic acid, percitric acid, perglycolic acid, perlactic acid, perbenzoic acid, and monoester peracids derived from diacids such as adipic, succinic, glutaric, or malonic acid and mixtures thereof, and mixtures thereof), phenolic derivatives (e.g., o-phenyl phenol, o-benzyl-p-chlorophenol and tert-amyl phenol), quaternary ammonium compounds (e.g., alkyldimethylbenzyl ammonium chloride, dialkyldimethyl ammonium chloride and mixtures thereof), and mixtures of such antimicrobial or biocidal agents, in an amount sufficient to provide the desired degree of microbial protection. Most of the aforementioned antimicrobial or biocidal agents having about 1–6 carbons, or an ionic charge, would be mostly soluble in the dilute phase; those with higher carbon numbers would generally be more solvent-phase soluble. In either case it is preferred to use antimicrobials that can be drawn into the solvent phase or onto surfaces during phase separation.

Compositions of the invention containing such antimicrobial or biocidal agents appear to have substantially greater effectiveness than corresponding compositions that do not exhibit phase-splitting behavior. If present in the concentrate, the antimicrobial or biocidal agent preferably is about 0.01 to about 30% of the concentrate, more preferably about 0.1 to about 10% and most preferably about 0.5 to about 5%.

If desired, the solvent compositions of the invention can contain various adjuvants such as chelants, builders, thickeners, fragrances, dyes, pH adjusters, anticorrosion additives and antirust additives. The types and amounts of such adjuvants will be apparent to those skilled in the art.

Although the solvent concentrates of the invention can be formulated to include the dilute phase liquid (e.g., water), preferably the concentrate contains little or no diluting liquid. The diluting liquid preferably is added at the time of use. A variety of dilution ratios can be employed, so long as the diluted composition exhibits the desired pseudo-stable and phase-splitting behaviors and is effective when applied to the chosen surface. The ingredients in the concentrate can represent about 1 to about 99% of the diluted mixture, more preferably about 5 to about 50%, and most preferably about 6 to about 25%.

Although no longer commercially available, an aqueous stripping agent concentrate previously sold in Canada as Fuller Formula 3100™ Super Concentrate (Fuller Brush, Quèbec) could be used in the present invention, if employed at a dilution ratio not recommended in the product instructions. Fuller Formula 3100™ Super Concentrate is believed to have contained about 49% benzyl alcohol, 17% monoethanolamine, 10% sodium decyldiphenyl ether disulfonate and 24% water. Dilution of the concentrate at a 1:20 concentrate:water ratio was recommended on the product instructions. At that dilution ratio, the resulting mixture formed a stable single-phase solution. However, if diluted at a sufficiently larger concentrate:water ratio (e.g., 1:10), the resulting mixture forms a pseudo-stable dispersion that will undergo phase splitting when applied to a substrate and allowed to stand for a few minutes.

Selection of the types and amounts of ingredients in the solvent compositions of the invention, and choice of an appropriate dilution ratio, preferably is accomplished by evaluating the cleaning, disinfecting, degreasing or stripping performance of the composition under representative test conditions. In general, stripping is more demanding than degreasing and most forms of cleaning or disinfecting. Stripping of UV-curable coatings is especially difficult, and thus represents a useful "worst-case" basis for such an evaluation. Stripping performance can be evaluated by coating and stripping tiles using the Substrate Coating Procedure and Stripping Evaluation Method (7 point scale) set out below in the Example section. Preferably, the compositions of the invention exhibit a rating of at least 3, and more preferably at least 6, when so evaluated.

The permeability of individual strip agent formulations of the invention through a multilayer coating can be graphically illustrated by applying several marked coats of metal-catalyzed acrylic floor finish and UV-curable coating to light colored floor tiles. A laundry marking pen or other suitable permanent felt marking pen is used to number each coat prior to application of the next coat. When the strip agent is applied to the resulting multilayer laminate construction, the applied numbers will fade away and disappear in the order in which the individual coats dissolve.

The compositions of the invention can be applied to surfaces using a variety of methods, including spraying, brushing, roll coating and flood coating. Mop application is preferred for coating floors. If a durable coating (e.g., a UV-crosslinked floor finish) is to be removed using a composition of the invention, removal can be assisted by applying the strip agent and then abrading the coating with a suitably mild abrasive (e.g., a green or black Scotch-Brite™ Floor Maintenance pad from 3M). The strip agent should be allowed to stand for a suitable time (e.g., for a minute or more, and typically between about 5 and about 30 minutes) while it forms split phases and attacks the coating. After the coating softens sufficiently (and after subjecting it to optional mild abrasion), the coating and strip agent can be removed from the floor or other surface using a variety of techniques including vacuuming, mopping or wiping. After removal of the coating and strip agent, the floor or other surface can optionally be rinsed with water or a suitable solvent to remove any remaining residue. The substrate can be allowed to dry and new layers of coating can be applied to renew the finish.

The compositions of the invention can be sold in the form of a kit containing the composition (e.g., a strip agent), together with suitable directions for carrying out the method of the invention. The kit can optionally contain one or more coating compositions that can be cleaned or removed using a composition of the invention. The kit can also optionally contain undercoat materials (e.g., leveling coatings) that can be applied to a substrate before application of the coating composition, overcoat materials (e.g., wax finishes) that can be applied atop the coating composition, and one or more applicators that can be used to apply the compositions of the invention to a surface.

The invention is further illustrated in the following non-limiting examples, in which all parts and percentages are by weight unless otherwise indicated. In the examples the following procedures were employed:

Substrate Coating Procedure

A set of 150 mm square white or black vinyl composite floor tiles from Armstrong Tile or from American Biltrite Limited was coated with 2 coats of a waterborne metal-catalyzed acrylic floor finish (Gemstar Laser™, Ecolab Inc.) applied at a 20% solids level. Each coat was allowed to air dry before application of the second coat. The total coating thickness after the second coat had dried was about 10 micrometers (at 5 micrometers per coat). The coated tiles were next coated with 2 coats of a waterborne UV curable coating formulation obtained from UV Coatings Limited (identified as "936-66-2", a 75:25 blend of an aliphatic polyester urethane and an acrylic resin) applied at a 30% solids level. Each coat was allowed to air dry before application of the next coat. The total dried coating thickness for these two UV curable coats was about 15 micrometers (at 7.5 micrometers per coat), yielding a combined coating thickness of about 25 micrometers. The coated tiles were passed through a UV curing apparatus containing an H bulb mercury vapor lamp operated at 1935 joule/sec per $cm^2$ and 4.9 meters per minute to cure the UV-curable topcoat layers.

EXAMPLE 1

A strip agent preconcentrate ("Preconcentrate A") was prepared by stirring 30 parts propylene glycol phenyl ether in a vessel and adding 30 parts diethylene glycol monobutyl ether (Butyl CELLOSOLVE™, Union Carbide Corp.) and 30 parts dipropylene glycol N-butyl ether. The mixture was stirred until it became uniform in appearance. Next, 10 parts of a C12–14 linear alcohol (9 mole) ethoxylate surfactant (Surfonic™ 24-9 ethoxylated alcohol, Huntsman Chemical) was added with stirring. The mixture formed a clear solution.

Preconcentrate A was combined with varying amounts of benzyl alcohol to form a series of 5 strip agent concentrates. The strip agent concentrates were diluted with water at a 1:9 concentrate:water ratio to form a series of 5 strip agents. All 5 strip agents formed cloudy solutions after mixing. The presence or absence of pseudo-stability was noted by observing whether phase-separation occurred within 5 minutes after mixing. A shorter or longer period could be chosen, but as noted above, 5 minutes represents a preferred pseudo-stability time.

The strip agents were applied to a UV-cured floor finish/metal-catalyzed floor finish laminate that had been coated on vinyl composite floor tiles using the Substrate Coating Procedure. The strip agent containing only benzyl alcohol and water separated very rapidly unless stirred continuously, and without such stirring could not be applied as a homogenous dispersion. The strip agents were visually observed to determine whether split phases formed following application of the strip agent to the tiles. Stripping performance was evaluated by allowing the strip agent to stand on the coated tiles for 10 minutes, abrading the strip agent with a green Scotch-Brite™ Floor Maintenance pad from 3M, attempting to remove the finish by mopping, and visually rating the degree of finish removal as "None", "Poor", "Partial" or "Complete". Set out below in Table I are the Run Number, ingredients in each strip agent concentrate, appearance upon mixing, presence or absence of pseudo-stability and split phases, and stripping performance for each strip agent and for a pure water control.

TABLE I

| Run No. | Preconcentrate A, parts | Benzyl Alcohol, parts | Appearance | Pseudo-Stability for 5 Minutes? | Split Phases? | Stripping Performance |
|---|---|---|---|---|---|---|
| 1-1 | 100 | 0 | Cloudy | No | No | Partial |
| 1-2 | 75 | 25 | Cloudy | No | No | Partial |
| 1-3 | 50 | 50 | Cloudy | No | Partial | Partial |
| 1-4 | 25 | 75 | Cloudy | Yes | Yes | Complete |
| 1-5 | 0 | 100 | Cloudy | No | Yes | Complete |
| 1-6 | 0 | 0 | Clear | No | No | None |

The results in Table I show that a pseudo-stable, phase splitting composition stripped a hard-to-remove UV-cured finish, and provided a water seal during stripping. Stripping could also be carried out using a 90:10 mixture of water and benzyl alcohol, but the composition could not be applied as a homogenous dispersion unless it was continuously stirred.

EXAMPLE 2

Using the method of Example 1, several 90:10 mixtures of benzyl alcohol and various emulsifying surfactants were combined to form strip agent concentrates. The strip agent concentrates were diluted with water at a 1:9 concentrate:water ratio to form a series of strip agents. All the strip agents formed cloudy solutions after mixing. The presence or absence of pseudo-stability was noted for each strip agent.

The strip agents were applied to a UV-cured floor finish/metal-catalyzed floor finish laminate and evaluated using the method of Example 1. Set out below in Table II are the Run Number, emulsifying surfactant (if any) added to each strip agent, appearance after mixing, presence or absence of pseudo-stability and split phases, and stripping performance for each strip agent.

TABLE II

| Run No. | Surfactant | Appearance | Pseudo-Stability for 5 Minutes? | Split Phases? | Stripping Performance |
|---|---|---|---|---|---|
| 2-1 | NPE[1] | Cloudy | No | No | Partial |
| 2-2 | DNPE[2] | Cloudy | No | No | None |
| 2-3 | L/M[3] | Cloudy | No | No | Partial |
| 2-4 | SXS[4] | Cloudy | No | No | None |
| 2-5 | HG[5] | Cloudy | No | No | None |
| 2-6 | None | Clear | No | Yes | Complete |

[1]Nonylphenol ethoxylate (4.5 EO)
[2]Dinonylphenol ethoxylate (10 EO)
[3]Laureth/Myristeth ethoxylate (7 EO)
[4]Sodium xylene sulfonate
[5]Hexylene glycol The results in Table II show that addition of excess surfactant prevented the formation of split phases and harmed stripping performance.

EXAMPLE 3

Using the method of Example 1, several strip agent concentrates were prepared by combining Preconcentrate A with varying amounts of methylethanolamine ("MEA") and benzyl alcohol. The strip agent concentrates were diluted with water at a 1:9 concentrate:water ratio to form a series of strip agents. The appearance after mixing was noted for each strip agent.

The strip agents were applied to a UV-cured floor finish/metal-catalyzed floor finish laminate and evaluated using the method of Example 1. Set out below in Table III are the Run Number, ingredients in each strip agent concentrate, presence or absence of split phases, and stripping performance for each strip agent.

TABLE III

| Run No. | Preconcentrate A, parts | MEA, parts | Benzyl Alcohol, parts | Appearance | Split Phases? | Stripping Performance |
|---|---|---|---|---|---|---|
| 3-1 | 100 | 0 | 0 | Cloudy | No | Partial |
| 3-2 | 75 | 25 | 0 | Cloudy | No | Partial |
| 3-3 | 50 | 50 | 0 | Cloudy | No | Partial |
| 3-4 | 25 | 75 | 0 | Cloudy | No | Poor |
| 3-5 | 0 | 100 | 0 | Clear | No | Poor |
| 3-6 | 0 | 75 | 25 | Clear | No | None |
| 3-7 | 0 | 50 | 50 | Clear | No | None |
| 3-8 | 0 | 25 | 75 | Cloudy | No | None |
| 3-9 | 0 | 0 | 100 | Cloudy | Yes | Complete |
| 3-10 | 50 | 25 | 25 | Milky | No | None |
| 3-11 | 25 | 50 | 25 | Cloudy | No | None |
| 3-12 | 25 | 25 | 50 | Milky | No | None |
| 3-13 | 75 | 12 | 13 | Cloudy | No | None |
| 3-14 | 12 | 75 | 13 | Cloudy | No | None |
| 3-15 | 12 | 13 | 75 | Milky | No | None |
| 3-16 | 33 | 33 | 34 | Milky | No | None |

The results in Table III show that a number of clear, cloudy or milky strip agent compositions could be formed, but that complete stripping performance was not obtained unless the strip agent exhibited phase splitting following application to a surface.

Various modifications and alterations of this invention will be apparent to those skilled in the art without departing from the scope and spirit of this invention. It should be understood that this invention is not limited to the illustrative embodiments set forth above.

We claim:

1. A pseudo-stable phase-splitting cleaning, antimicrobial, degreasing or stripping solvent composition that forms at least two phases promptly after being applied atop a generally horizontal surface or on a generally vertical surface, whereby a film containing a concentrated amount of the solvent lies between the surface and a film containing a much lower amount of the solvent.

2. A composition according to claim 1, wherein the solvent comprises a polar solvent.

3. A composition according to claim 2, wherein the polar solvent is at least one or more of an ether, an aromatic alcohol, a dialkyl diester, or mixtures thereof.

4. A composition according to claim 2, wherein the polar solvent is at least one or more of benzyl alcohol, ethylene glycol phenyl ether, propylene glycol phenyl ether, propylene carbonate, phenoxyethanol, dimethyl adipate, dimethyl succinate, dimethyl glutarate, dimethyl malonate, diethyl adipate, diethyl succinate, diethyl glutarate, dibutyl adipate, dibutyl succinate, dibutyl glutarate, or mixtures hereof.

5. A composition according to claim 1, wherein the composition is an antimicrobial composition or contains another antimicrobial or biocidal agent dissolved or dispersed in the solvent.

6. A composition according to claim 1, wherein the composition contains water, and the solvent is more dense than water.

7. A composition according to claim 6, wherein when the composition is mixed it has a pseudo-stable emulsified state that lasts for at least one minute or more after mixing while the composition is stored in a bucket or other vessel, and wherein when the composition is applied to a surface it will phase-separate to form a predominantly solvent-containing layer on the surface.

8. A composition according to claim 7, wherein the surface is at least one or more of a hard surface, soft surface, porous surface, food substance or skin.

9. A composition according to claim 8, wherein the surface comprises an architectural surface.

10. A composition according to claim 9, wherein the architectural surface is at least one or more of a floor, wall, window, sink, table, counter or bathroom.

11. A composition according to claim 8, wherein the surface is at least one or more of a medical or surgical instrument or device, a transportation vehicle, or an eating utensil.

12. A composition according to claim 8, wherein the surface comprises a porous surface.

13. A composition according to claim 12, wherein the porous surface comprises paper or fabric.

14. A composition according to claim 8, when the surface comprises a floor.

15. A composition according to claim 14, wherein the composition will phase-separate within two minutes after application.

16. A composition according to claim 7, wherein the surface comprises a crosslinked polymeric topcoat.

17. A composition according to claim 6, wherein the solvent has a water solubility less than about 10% by weight.

18. A composition according to claim 6, wherein the solvent has a water solubility less than about 5% by weight.

19. A composition according to claim 6, wherein the solvent has a water solubility less than about 1% by weight.

20. A composition according to claim 1, further comprising cosolvent or surfactant.

21. A composition according to claim 20, wherein the cosolvent has greater water solubility than the solvent.

22. A composition according to claim 20, containing water and at least about 10% solvent.

23. A composition according to claim 20, containing water and at least about 50 weight % solvent.

24. A composition according to claim 20, containing about 75 weight % to about 95 weight % solvent.

25. A pseudo-stable phase-splitting cleaning, antimicrobial, degreasing or stripping solvent composition, wherein the composition contains about 75 weight % to about 95 weight % solvent and the solvent comprises benzyl alcohol, ethylene glycol phenyl ether, phenoxyethanol, or propylene glycol phenyl ether, and the composition further comprises cosolvent or surfactant, contains about 5 weight % to about 25 weight % cosolvent comprising diethylene glycol monobutyl ether or dipropylene glycol N-butyl ether, and contains no more than about 3 weight % surfactant.

* * * * *

UNITED STATES PATENT AND TRADEMARK OFFICE
CERTIFICATE OF CORRECTION

PATENT NO. : 6,544,942 B1　　　　　　　　　　　　　　　　　　　　　　　　Page 1 of 1
DATED       : April 8, 2003
INVENTOR(S) : Smith et al.

It is certified that error appears in the above-identified patent and that said Letters Patent is hereby corrected as shown below:

Title page,
Item [75], Inventors, after "Robert D. P. Hei, Baldwin, WI (US)" the listed inventors should include -- Keith E. Olson, Apple Valley, MN (US)
　　　　　　　Bryan M. Anderson, Saint Paul, MN (US) --.

Column 5,
Item 33, "1.0413); benzyl" should read -- 1.04); benzyl --.

Column 8,
Line 10, "nis" should read -- n is --.

Signed and Sealed this

Eighteenth Day of October, 2005

JON W. DUDAS
*Director of the United States Patent and Trademark Office*